United States Patent [19]

Lee

[11] 4,254,116
[45] Mar. 3, 1981

[54] 5H-[1]BENZOPYRANO[3,4-d]PYRIDINES

[75] Inventor: Cheuk M. Lee, Waukegan, Ill.

[73] Assignee: Abbott Laboratories, North Chicago, Ill.

[21] Appl. No.: 458,744

[22] Filed: Apr. 8, 1974

Related U.S. Application Data

[63] Continuation-in-part of Ser. No. 379,016, Jul. 13, 1973, Pat. No. 3,878,219.

[51] Int. Cl.³ .................. A61K 31/54; C07D 491/052; A61K 31/435; A61K 31/495
[52] U.S. Cl. .................................... 424/246; 546/89; 544/126; 544/58.6; 544/375; 424/256; 424/248.54; 424/250
[58] Field of Search ..................... 260/243 B, 247.2 B, 260/268 TR, 293.58, 295 T, 296 H; 546/89; 544/126, 58.1–58.5, 375; 424/256, 248.54, 250, 246

[56] References Cited

U.S. PATENT DOCUMENTS

| | | | |
|---|---|---|---|
| 3,429,889 | 2/1969 | Shulgin | 260/295 |
| 3,514,464 | 5/1970 | Pars et al. | 260/295 |
| 3,632,595 | 1/1972 | Pars et al. | 260/297 H |
| 3,661,919 | 5/1972 | Razdan et al. | 260/297 R |
| 3,787,424 | 1/1974 | Pars et al. | 260/295 T |

*Primary Examiner*—Henry R. Jiles
*Assistant Examiner*—Robert C. Whittenbaugh
*Attorney, Agent, or Firm*—Robert L. Niblack

[57] ABSTRACT

5H-[1]Benzopyrano[3,4-d]pyridines represented by the formula

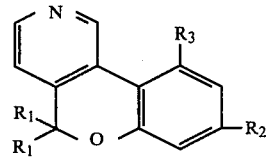

wherein each $R_1$ is loweralkyl, $R_2$ is alkyl, cycloalkyl or

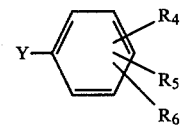

wherein Y is a straight or branched chain alkylene group having from 1 to 10 carbon atoms and each $R_4$, $R_5$ and $R_6$ are the same or different members of the group consisting of hydrogen, halo, trifluoromethyl or loweralkyl; and $R_3$ is hydroxy, acyloxy, loweralkoxy, loweralkenyloxy, loweralkynyloxy or

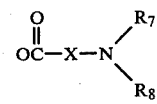

X is a straight or branched chain alkylene group having from one to eight carbon atoms, and wherein $R_7$ and $R_8$ are the same or different members of the group consisting of hydrogen or loweralkyl, or

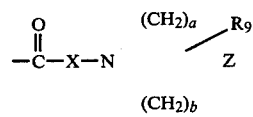

wherein X is a straight or branched chain alkylene group having from one to eight carbon atoms, a is an integer from 1 to 4, b is an integer from 1 to 4, Z is $CH_2$, O, S or $NR_{10}$ with $R_{10}$ being hydrogen or loweralkyl, with the limitation that when Z is O or S, the sum of a and b is 3 or 4; and when Z is $NR_{10}$, the sum of a and b is 3–5; $R_9$ is hydrogen or loweralkyl, and the pharmaceutically acceptable salts thereof.

23 Claims, No Drawings

5H-[1]BENZOPYRANO[3,4-D]PYRIDINES

CROSS-REFERENCE TO RELATED APPLICATION

This application is a continuation-in-part of copending application, Ser. No. 379,016 filed July 13, 1973 now U.S. Pat. No. 3,878,219.

DETAILED DESCRIPTION OF THE INVENTION

This invention relates to novel benzopyrans and more particularly relates to 5H-[1]benzopyrano[3,4-d]pyridines represented by the formula

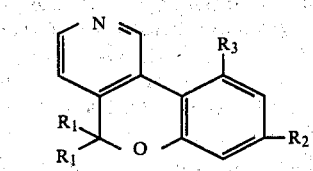

wherein each $R_1$ is loweralkyl, $R_2$ is alkyl, cycloalkyl or

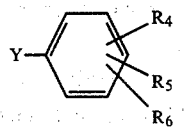

wherein Y is a straight or branched chain alkylene group having from 1 to 10 carbon atoms and each $R_4$, $R_5$ and $R_6$ are the same or different members of the group consisting of hydrogen, halo, trifluoromethyl or loweralkyl; and $R_3$ is hydroxy, acyloxy, loweralkoxy, loweralkenyloxy, loweralkynyloxy or

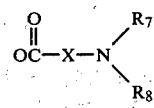

X is a straight or branched chain alkylene group having from one to eight carbon atoms, and wherein $R_7$ and $R_8$ are the same or different members of the group consisting of hydrogen or loweralkyl, or

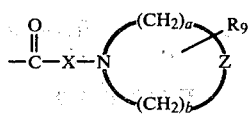

wherein X is a straight or branched chain alkylene group having from one to eight carbon atoms, a is an integer from 1 to 4, b is an integer from 1 to 4, Z is $CH_2$, O, S or $NR_{10}$ with $R_{10}$ being hydrogen or loweralkyl, with the limitation that when Z is O or S, the sum of a and b is 3 or 4; and when Z is $NR_{10}$, the sum of a and b is 3–5; $R_9$ is hydrogen or loweralkyl, and the pharmaceutically acceptable salts thereof.

As used herein, the term "loweralkyl" refers to $C_1$–$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "alkyl" refers to straight and branched chain alkyl radicals having from one to twenty carbon atoms such as methyl, n-amyl, 3-methyl-2-octyl, 2-nonyl, 2-eicosanyl and the like.

"Cycloalkyl", as used herein, refers to cyclic saturated aliphatic radicals having three to eight carbon atoms in a ring, such as cyclopropyl, cyclobutyl, cyclopentyl, cyclohexyl, cycloheptyl and cyclooctyl.

The term "halo" includes chloro, fluoro, bromo and iodo.

The term "acyloxy" refers to acetoxy, propionyloxy, butyryloxy and the like.

The term "loweralkoxy" refers to a loweralkyl group connected to an oxygen such as: methoxy, ethoxy, propyloxy, butoxy and the like.

The term "lower alkenyloxy" refers to 2-propenyloxy, (3-methyl-2-propenyl)oxy and (1,3-dimethyl-2-propenyl)oxy.

The term "lower alkynyloxy" includes 2-propynyloxy (3-methyl-2-propynyl)oxy and (1-methyl-2-propynyl)oxy.

When $R_3$ is an ester, the term "pharmaceutically acceptable salts" refers to acid addition salts prepared by reacting the basic esters of the benzopyrans with an organic or inorganic acid, or by reacting the benzopyrans with the salt of an appropriate acid. When $R_3$ is hydroxy, the term refers to alkali metal, alkaline earth metal, ammonium and substituted ammonium salts such as hydrochloride, hydrobromide, sulfate, bisulfate, acetate, valerate, oleate, laurate, borate, benzoate, lactate, phosphate, tosylate, citrate, maleate, succinate, tartrate, napsylate and the like.

When $R_3$ is hydroxy, the compounds of this invention are prepared by dehydrogenation of the corresponding 1,2,3,4-tetrahydro-5H[1]benzopyrano[3,4-d]pyridine with, for example, palladium on carbon in a boiling inert solvent, or by debenzylation and dehydrogenation of the corresponding N-benzyl 1,2,3,4-tetrahydro compound. When $R_3$ is hydroxy, and $R_2$ is alkyl or cycloalkyl, the tetrahydro compounds can be prepared according to the method described in U.S. Pat. No. 3,576,798. When $R_3$ is hydroxy, and $R_2$ is

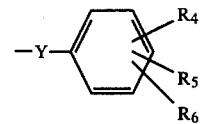

the compounds are prepared according to the following reaction scheme:

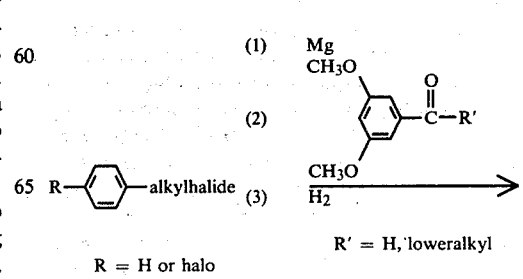

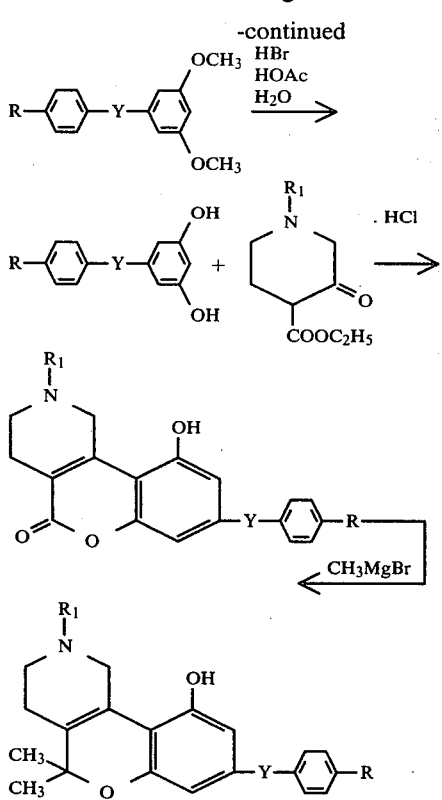

Compounds wherein $R_3$ is acyloxy are prepared by reacting the corresponding compound wherein $R_3$ is hydroxy with the appropriate acyl anhydride such as acetic anhydride.

The esters of this invention, $R_3=$

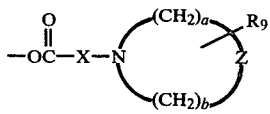

are prepared by reacting equimolar quantities of the corresponding benzopyranopyridine, and the appropriate acid or its salt, in the presence of a carbodiimide such as dicyclohexyl carbodiimide, in a suitable solvent such as methylene chloride, chloroform and the like.

Some of the heterocyclic acids which can be used in the process are:
γ-piperidinobutyric acid,
γ-morpholinobutyric acid,
γ-(2-methylpiperidino)-butyric acid,
δ-piperidinovaleric acid,
γ-pyrrolidinobutyric acid,
β-piperidinopropionic acid,
γ-thiomorpholinobutyric acid and
homopiperidinoacetic acid Reaction between the benzopyranopyridine starting material and the heterocyclic acid, or salt thereof, is readily effected by combining about equimolar amounts of the reactants and a slight excess of a carbodiimide such as dicyclohexylcarbodiimide. The reaction proceeds readily at room temperature and is generally completed in about 4 to 20 hours. After the reaction is terminated, the reaction mixture can be filtered to remove the by-product of dicyclohexylurea, and the solvent can be distilled off using a rotary evaporator. The residue can be directly crystallized from a suitable solvent such as benzene/ether or the residue can be chromatographed and the desired material isolated from the appropriate chromatographic fractions. If the basic esters are obtained, the acid addition salts such as those named above, if desired, can be prepared by methods well known in the art.

The compounds of this invention, in the form of the free bases, can be used as neutralizing agents since they form salts with acids.

The pharmacological activity of the compounds of this invention renders them useful as drugs although it should be understood that every compound of the invention will not necessarily have each activity possessed by the others.

The compounds of this invention are useful as analgesic agents, and generally at dosages of from 1 to 10 mg./kg. of body weight daily. The analgesic activity was established in the standard mouse writhing test [Whittle, *Brit. J. Pharmacol.*, 22, 296 (1964)] and confirmed in the hot plate assay [Woolfe, G. and MacDonald, A. D., *J. Pharmacol. Exper. Therap.*, 80, 300, (1944)] and the rat tail flick test [D'Amour and Smith, *J. Pharmacol. Exper. Therap.*, 72: 74, (1941)]. The compounds are additionally useful as antianxiety agents and antidepressant agents.

The following examples further illustrate this invention:

EXAMPLE 1

5,5-Dimethyl-10-hydroxy-8-(3-methyl-2-octyl)-5H-[1]benzopyrano[3,4-d]pyridine

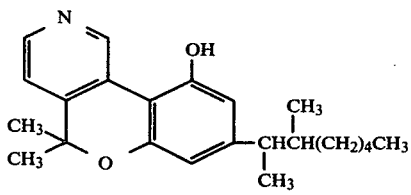

A mixture of 4.20 g. of 5,5-dimethyl-10-hydroxy-8-(3-methyl-2-octyl)-1,2,3,4-tetrahydro-5H-[1]benzopyrano[3,4-d]pyridine, 0.8 g. of 10% palladium on carbon and 80 ml. of xylene was stirred and refluxed for 25 hours. After cooling, the catalyst was removed by filtration. The filtrate was evaporated in vacuo and the product was recrystallized from autonitrile; m.p. 155°–157°.

Calcd. for $C_{23}H_{31}NO_2$: C, 78.14; H, 8.84; N, 3.97. Found: C, 77.93; H, 9.00; N, 3.85.

EXAMPLE 2

5,5-Dimethyl-10-hydroxy-8-methyl-5H-[1]benzopyrano[3,4-d]pyridine is prepared by dehydrogenating 5,5-dimethyl-10-hydroxy-8-methyl-1,2,3,4-tetrahydro-5H-[1]benzopyrano[3,4-d]pyridine following the procedure of Example 1.

EXAMPLE 3

5,5-Dimethyl-10-hydroxy-8-(1-pentyl)-5H-[1]benzopyrano[3,4-d]pyridine is prepared by dehydrogenating 5,5-dimethyl-10-hydroxy-8-(1-pentyl)-1,2,3,4-tetrahydro-5H-[1]benzopyrano[3,4-d]pyridine following the procedure of Example 1.

EXAMPLE 4

5,5-Dimethyl-10-hydroxy-8-(2-heptyl)-5H-[1]benzopyrano[3,4-d]pyridine is prepared by dehydrogenating 5,5-dimethyl-10-hydroxy-8-(2-heptyl)-1,2,3,4-tetrahydro-5H-[1]benzopyrano[3,4-d]pyridine following the procedure of Example 1.

EXAMPLE 5

5,5-Dimethyl-10-hydroxy-8-(1-cyclohexylethyl)-5H-[1]benzopyrano[3,4-d]pyridine is prepared by dehydrogenating 5,5-dimethyl-10-hydroxy-8-(1-cyclohexylethyl)-1,2,3,4-tetrahydro-5H-[1]benzopyrano[3,4-d]pyridine following the procedure of Example 1.

EXAMPLE 6

5,5-Dimethyl-10-hydroxy-8-(3-cyclopropyl-2-propyl)-5H-[1]benzopyrano[3,4-d]pyridine is prepared by dehydrogenating 5,5-dimethyl-10-hydroxy-8-(3-cyclopropyl-2-propyl)-1,2,3,4-tetrahydro-5H-[1]benzopyrano[3,4-d]pyridine following the procedure of Example 1.

EXAMPLE 7

5,5-Dimethyl-10-hydroxy-8-(2-tetradecyl)-5H-[1]benzopyrano[3,4-d]pyridine is prepared by dehydrogenating 5,5-dimethyl-10-hydroxy-8-(2-tetradecyl)-1,2,3,4-tetrahydro-5H-[1]benzopyrano[3,4-d]pyridine following the procedure of Example 1.

EXAMPLE 8

5,5-Dimethyl-10-hydroxy-8-(2-eicosyl)-5H-[1]benzopyrano[3,4-d]pyridine is prepared by dehydrogenating 5,5-dimethyl-10-hydroxy-8-(2-eicosyl)-1,2,3,4-tetrahydro-5H-[1]benzopyrano[3,4-d]pyridine following the procedure of Example 1.

EXAMPLE 9

5,5-Dimethyl-10-hydroxy-8-ethyl-5H-[1]benzopyrano[3,4-d]pyridine is prepared by dehydrogenating 5,5-dimethyl-10-hydroxy-8-ethyl-1,2,3,4-tetrahydro-5H-[1]benzopyrano[3,4-d]pyridine following the procedure of Example 1.

EXAMPLE 10

5,5-Dimethyl-10-hydroxy-8-iso-propyl-5H-[1]benzpyrano[3,4-d]pyridine is prepared by dehydrogenating 5,5-dimethyl-10-hydroxy-8-iso-propyl-1,2,3,4-tetrahydro-5H-[1]benzopyrano[3,4-d]pyridine following the procedure of Example 1.

EXAMPLE 11

5,5-Dimethyl-10-hydroxy-8-(2-hexyl)-5H-[1]benzopyrano[3,4-d]pyridine is prepared by dehydrogenating 5,5-dimethyl-10-hydroxy-8-(2-hexyl)-1,2,3,4-tetrahydro-5H-[1]benzopyrano[3,4-d]pyridine following the procedure of Example 1.

EXAMPLE 12

10-Acetoxy-5,5-dimethyl-8-(3-methyl-2-octyl)-5H-[1]benzopyrano[3,4-d]pyridine

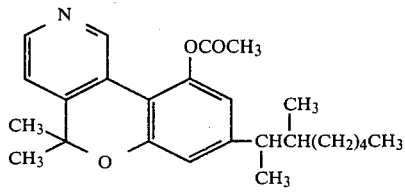

A mixture of 3.53 g. (0.01 mole) of 5,5-dimethyl-10-hydroxy-8-(3-methyl-2-octyl)-5H-[1]benzopyrano[3,4-d]pyridine, 1.22 g. (0.012 mole) of acetic anhydride, and 5 ml. of pyridine was stirred at room temperature for 24 hours. The reaction mixture was evaporated in vacuo, and the residue was taken up in ether. The ether solution was washed with water, dried with anhydrous sodium sulfate, and evaporated in vacuo. The residue was purified by chromatography on a Florosil ® activated aluminum magnesium silicate 22 mm×30 inch column with chloroform to give the pure product.

Calcd. for $C_{25}H_{33}NO_3$: C, 75.91; H, 8.41; N, 3.54. Found: C, 75.62; H, 8.52; N, 3.38.

EXAMPLE 13

10-Acetoxy-5,5-dimethyl-8-ethyl-5H-[1]benzopyrano[3,4-d]pyridine is prepared by reacting 5,5-dimethyl-10-hydroxy-8-ethyl-5H-[1]benzopyrano[3,4-d]pyridine and acetic anhydride in the presence of pyridine according to the method of Example 12.

EXAMPLE 14

10-Acetoxy-5,5-dimethyl-8-n-pentyl-5H-[1]benzopyrano[3,4-d]pyridine is prepared by reacting 5,5-dimethyl-10-hydroxy-8-n-pentyl-5H-[1]benzopyrano[3,4-d]pyridine and acetic anhydride in the presence of pyridine according to the method of Example 12.

EXAMPLE 15

10-Acetoxy-5,5-dimethyl-8-(2-heptyl)-5H-[1]benzopyrano[3,4-d]pyridine is prepared by reacting 5,5-dimethyl-10-hydroxy-8-(2-heptyl)-5H-[1]benzopyrano[3,4-d]pyridine and acetic anhydride in the presence of pyridine according to the method of Example 12.

EXAMPLE 16

10-Acetoxy-5,5-dimethyl-8-(1-cyclohexylethyl)-5H-[1]benzopyrano[3,4-d]pyridine is prepared by reacting 5,5-dimethyl-10-hydroxy-8-(1-cyclohexylethyl)-5H-[1]benziopyrano[3,4-d]pyridine and acetic anhydride in the presence of pyridine according to the method of Example 12.

EXAMPLE 17

10-Acetoxy-5,5-dimethyl-8-(3-cyclopropyl-2-propyl)-5H-[1]benzopyrano[3,4-d]pyridine is prepared by reacting 5,5-dimethyl-10-hydroxy-8-(3-cyclopropyl-2-propyl)-5H-[1]benzopyrano[3,4-d]pyridine and acetic anhydride in the presence of pyridine according to the method of Example 12.

EXAMPLE 18

10-Acetoxy-5,5-dimethyl-8-(2-tetradecyl)-5H-[1]benzopyrano[3,4-d]pyridine is prepared by reacting 5,5-dimethyl-10-hydroxy-8-(2-tetradecyl)-5H-[1]benzopyrano[3,4-d]pyridine and acetic anhydride in the presence of pyridine according to the method of Example 12.

EXAMPLE 19

10-Acetoxy-5,5-dimethyl-8-(2-eicosyl)-5H-[1]benzopyrano[3,4-d]pyridine is prepared by reacting 5,5-dimethyl-10-hydroxy-8-(2-eicosyl)-5H-[1]benzopyrano[3,4-d]pyridine and acetic anhydride in the presence of pyridine according to the method of Example 12.

EXAMPLE 20

10-Acetoxy-5,5-dimethyl-8-n-butyl-5H-[1]benzopyrano[3,4-d]pyridine is prepared by reacting 5,5-dimethyl-10-hydroxy-8-n-butyl-5H-[1]benzopyrano[3,4-d]pyridine and acetic anhydride in the presence of pyridine according to the method of Example 12.

EXAMPLE 21

10-Acetoxy-5,5-dimethyl-8-iso-propyl-5H-[1]benzopyrano[3,4-d]pyridine is prepared by reacting 5,5-dimethyl-10-hydroxy-8-iso-propyl-5H-[1]benzopyrano[3,4-d]pyridine and acetic anhydride in the presence of pyridine according to the method of Example 12.

EXAMPLE 22

10-Acetoxy-5,5-dimethyl-8-(2-hexyl)-5H-[1]benzopyrano[3,4-d]pyridine is prepared by reacting 5,5-dimethyl-10-hydroxy-8-(2-hexyl)-5H-[1]benzopyrano[3,4-d]pyridine and acetic anhydride in the presence of pyridine according to the method of Example 12.

EXAMPLE 23

Preparation of 2-(3,5-dimethoxyphenyl)-5-(4-fluorophenyl) pentane

A solution of 77 g. of 3-(4-fluorophenyl)propylbromide in 300 ml. of ether was added dropwise over a 2 hour period to a refluxing solution of 10 g. of magnesim in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl)-propylbromide was worked up in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-fluorophenyl)pentane, b.p. 145–155/0.05 mmHg.

Analysis Calcd. for $C_{19}H_{23}O_2F$: C, 75.60; H, 7.69. Found: C, 75.87; H, 7.98.

EXAMPLE 24

Preparation of 2-(3,5-dihydroxyphenyl)-5-(4-fluorophenyl)pentane

Fifty grams of the above prepared 2-(3,5-dimethoxyphenyl)-5-(4-fluorophenyl)pentane, 450 ml. of acetic acid and 180 ml. of 48% HBr in water were mixed. While cooling, the mixture was saturated with hydrogen bromide gas (approximately ½ hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(4-fluorophenyl)pentane as a brown oil which distills at 180°/0.01 mmHg.

Analysis Calcd. for $C_{17}H_{25}O_2F$: C, 74.20; H, 6.98. Found: C, 73.56; H, 7.04.

EXAMPLE 25

Preparation of 2-Benzyl-8-[5-(4-fluorophenyl)-2-pentyl]-10-hydroxy-5-oxo-1,2,3,4-tetrahydro-5H-[1]benzopyrano[3,4-d]pyridene hydrochloride To 45 g. of 2-(3,5-dihydroxyphenyl)-5-(4-fluorophenyl)pentane dissolved in 100 ml. of methanesulfonic acid were added in portions, 57 g. of 1-benzyl-3-keto-4-carbethoxy piperidine hydrochloride. While stirring, 68 g. of $POCl_3$ were added and the solution was stirred for 5 days at room temperature. Water (300 ml.) and 180 ml. of $CHCl_3$ were then added and the reaction mixture stirred for 30 minutes. After the addition of 100 ml. of 15% NaOH, the reaction was stirred for an additional ten (10) minutes. The $CHCl_3$ layer was separated and extracted with 10% HCl. The $CHCl_3$ layer was concentrated and $CH_3CN$ added thereto to yield 55 g. of the desired product as the hydrochloride salt, m.p. 254°–256° C.

Analysis Calcd. for: C, 70.80; H, 6.14; Cl, 6.97; N, 2.75. Found: C, 70.15; H, 6.17; Cl, 7.23; N, 2.74.

EXAMPLE 26

Preparation of 2-Benzyl-5,5-dimethyl-8-[5-(4-fluorophenyl)-2-pentyl]-10-hydroxy-1,2,3,4-tetrahydro-5H[1]benzopyrano[3,4-d]pyridine Sixty five grams of the above-prepared 2-Benzyl-8-[5-(4-fluorophenyl)-2-pentyl]-10-hydroxy-5-oxo-1,2,3,4-tetrahydro-5H[1]benzopyrano[3,4-d]pyridine hydrochloride were suspended in 300 ml. of $CHCl_3$. After adding a $KHCO_3$ solution, the reaction was stirred for 30 minutes. The chloroform layer was separated, dried over $MgSO_4$, concentrated taken up in benzene and concentrated again. The concentrate was taken up in 185 ml. of hot anisole and the resulting solution was added dropwise to a solution of $CH_3MgBr$ in anisole (prepared by adding 180 g. of $CH_3Br$ in 500 ml. of ether to 40 g. of Mg in 150 ml. of ether, evaporating the ether and adding 300 ml. of anisole). The reaction mixture was stored overnight at 62° C. Water (200 ml.) was added slowly, followed by 400 ml. of 10% $H_2SO_4$. The anisole was removed by steam distillation and the resulting solid was taken up in chloroform, neutralized with $KHCO_3$, dried over $MgSO_4$, concentrated and the product (36.5 g.), m.p. 188°–190° C., crystallized from $CH_3CN$.

EXAMPLE 27

5,5-Dimethyl-8-[5-(4-fluorophenyl)-2-pentyl]-10-hydroxy-5H-[1]benzopyrano[3,4-d]pyridine

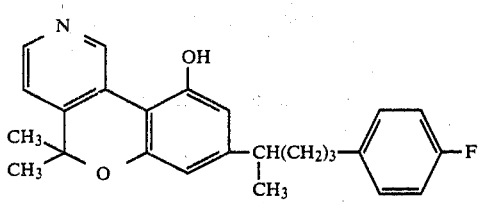

A mixture of 4.75 g. of 5,5-dimethyl-8-[5-(4-fluorophenyl)-2-pentyl]-10-hydroxy-1,2,3,4-tetrahydro-5H-[1]benzopyrano[3,4-d]pyridine, 1.0 g. of 10% palladium on carbon, and 120 ml. of xylene was stirred and refluxed for 22 hours. After removal of the catalyst, the filtrate was evaporated in vacuo and the residue was purified by chromatography on a Florisil column (150 g.). The column was first eluted with chloroform, followed by 5% methanol in chloroform to give the pure product; m.p. 72°–74°.

Calcd. for $C_{25}H_{26}FNO_2$: C, 76.69; H, 6.70; N, 3.58. Found: C, 77.12; H, 7.15; N, 3.61.

EXAMPLE 28

5,5-Dimethyl-8-[5-phenyl-2-pentyl]-10-hydroxy-5H[1]benzopyrano[3,4-d]pyridine is prepared from 5,5-dimethyl-8-[5-phenyl-2-pentyl]-10-hydroxy-1,2,3,4-tetrahydro-5H[1]benzopyrano[3,4-d]pyridine following the procedure of Example 27.

EXAMPLE 29

5,5-Dimethyl-8-(3-methyl-2-octyl)-10-[4-(piperidino)-butyryloxy]-5H-[1]benzopyrano[3,4-d]pyridine hydrochloride

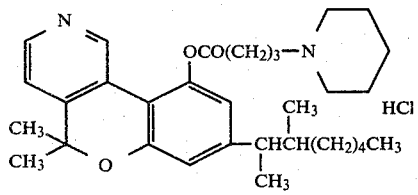

A mixture of 3.53 g. (0.01 mole) of 5,5-dimethyl-10-hydroxy-8-(3-methyl-2-octyl)-5H-[1]benzopyrano[3,4-d]pyridine, 2.07 g. (0.01 mole) of γ-piperidinobutyric acid hydrochloride, 2.16 g. (0.0105 mole) of N,N'-dicyclohexylcarbodiimide, and 160 ml. of dried methylene chloride was stirred overnight at room temperature. The reaction mixture was cooled at approximately 5° C. for several hours and was filtered to remove dicyclohexylurea. The filtrate was evaporated in vacuo and the residue was dissolved in 12.5 ml. of methylene chloride and 50 ml. of cyclohexane. After standing overnight in the cold room (approximately 5° C.), the mixture was filtered again and the filtrate was evaporated in vacuo. The residue was recrystallized from methylene chloride/ether, giving 4.1 g. of the product, m.p. 134°–137°.

Calcd. for: $C_{32}H_{46}N_2O_3 \cdot HCl$: C, 70.76; H, 8.72; N, 5.16. Found: C, 70.71; H, 8.91; N, 5.21.

EXAMPLE 30

5,5-Dimethyl-8-(1-pentyl)-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-(1-pentyl)-5H-[1]benzopyrano[3,4-d]pyridine and γ-piperidinobutyric acid hydrochloride in the presence of dicyclohexylcarbodiimide.

EXAMPLE 31

5,5-Dimethyl-8-(2-heptyl)-10-[4-(piperidino)-butyryloxy]-5H-[1]benzopyrano[3,4-d]pyridine hydrochloride is prepared according to the method of Example 29 by reacting equimolar quantities of 5,5-dimethyl-8-(2-heptyl)-10-hydroxy-5H[1]benzopyrano[3,4-d]pyridine and γ-piperidinobutyric acid hydrochloride in the presence of dicyclohexyl carbodiimide.

EXAMPLE 32

5,5-Dimethyl-8-(1-cyclohexylethyl)-10-[4-(piperidino)butyryloxy]-5H-[1]benzopyrano[3,4-d]pyridine hydrochloride is prepared according to the method of Example 29 by reacting equimolar quantities of 5,5-dimethyl-10-hydroxy-8-(1-cyclohexylethyl)-5H[1]benzopyrano[3,4-d]pyridine and γ-piperidinobutyric acid hydrochloride in the presence of dicyclohexyl carbodiimide.

EXAMPLE 33

5,5-Dimethyl-8-(3-cyclopropyl-2-propyl)-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-(3-cyclopropyl-2-propyl)-5H-[1]benzopyrano[3,4-d]pyridine and γ-piperidinobutyric acid hydrochloride in the presence of dicyclohexyl-carbodiimide.

EXAMPLE 34

5,5-Dimethyl-8-(2-tetradecyl)-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-(2-tetradecyl)-5H-[1]benzopyrano[3,4-d]pyridine and γ-piperidinobutyric acid hydrochloride in the presence of dicyclohexyl carbodiimide.

EXAMPLE 35

5,5-Dimethyl-8-(2-eicosyl)-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-(2-eicosyl)-5H-[1]benzopyrano[3,4-d]pyridine and γ-piperidinobutyric acid hydrochloride in the presence of dicyclohexyl carbodiimide.

EXAMPLE 36

5,5-Dimethyl-8-ethyl-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-ethyl-5H-[1]benzopyrano[3,4-d]pyridine and γ-piperidinobutyric acid hydrochloride in the presence of dicyclohexyl carbodiimide.

EXAMPLE 37

5,5-Dimethyl-8-methyl-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-methyl-5H-[1]benzopyrano[3,4-d]pyridine and γ-piperidinobutyric acid hydrochloride in the presence of dicyclohexyl carbodiimide.

EXAMPLE 38

5,5-Dimethyl-8-iso-propyl-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-iso-propyl-5H-[1]benzopyrano[3,4-d]pyridine and γ-piperidinobutyric acid hydrochloride in the presence of dicyclohexyl carbodiimide.

EXAMPLE 39

5,5-Dimethyl-8-(2-hexyl)-10-[4-(piperidino)-butyryloxy]-5H-[1]benzopyrano[3,4-d]pyridine hydrochloride is prepared according to the method of Example 29 by reacting equimolar quantities of 5,5-dimethyl-10-hydroxy-8-(2-hexyl)-5H-[1]benzopyrano[3,4-d]pyridine and γ-piperidinobutyric acid hydrochloride in the presence of dicyclohexyl carbodiimide.

EXAMPLE 40

5,5-Dimethyl-8-[5-phenyl-2-pentyl]-10-[4-(piperidino)butyryloxy]-5H-[1]benzopyrano[3,4-d]pyridine hydrochloride is prepared according to the method of Example 29 by reacting equimolar quantities of 5,5-dimethyl-10-hydroxy-8-[5-phenyl-2-pentyl]-5H-[1]benzopyrano[3,4-d]pyridine and γ-piperidinobutyric acid hydrochloride in the presence of dicyclohexyl carbodiimide.

EXAMPLE 41

5,5-Dimethyl-8-(3-methyl-2-octyl)-10-[4-(morpholino)butyryloxy]-5H-[1]benzopyrano[3,4-d]pyridine hydrochloride is prepared according to the method of Example 29 by reacting equimolar quantities of 5,5-dimethyl-10-hydroxy-8-(3-methyl-2-octyl)-5H-[1]benzopyrano[3,4-d]pyridine and γ-morpholinobutyric acid hydrochloride in the presence of dicyclohexyl carbodiimide.

EXAMPLE 42

5,5-Dimethyl-8-(3-methyl-2-octyl)-10-[4-(pyrrolidino)butyryloxy]-5H-[1]benzopyrano[3,4-d]pyridine hydrochloride is prepared according to the method of Example 29 by reacting equimolar quantities of 5,5-dimethyl-10-hydroxy-8-(3-methyl-2-octyl)-5H-[1]benzopyrano[3,4-d]pyridine and γ-pyrrolidinobutyric acid hydrochloride in the presence of dicyclohexyl carbodiimide.

EXAMPLE 43

5,5-Dimethyl-8-(3-methyl-2-octyl)-10-[4-(2-methylpiperidino)butyryloxy]-5H-[1]benzopyrano[3,4-d]pyridine hydrochloride is prepared according to the method of Example 29 by reacting equimolar quantities of 5,5-dimethyl-10-hydroxy-8-(3-methyl-2-octyl)-5H-[1]benzopyrano[3,4-d]pyridine and γ-(2-methylpiperidino)butyric acid hydrochloride in the presence of dicyclohexyl carbodiimide.

EXAMPLE 44

5,5-Dimethyl-8-(3-methyl-2-octyl)-10-[5-(piperidino)valeryloxy]-5H-[1]benzopyrano[3,4-d]pyridine hydrochloride is prepared according to the method of Example 29 by reacting equimolar quantities of 5,5-dimethyl-10-hydroxy-8-(3-methyl-2-octyl)-5H-[1]benzopyrano[3,4-d]pyridine and δ-piperidinovaleric acid hydrochloride in the presence of dicyclohexyl carbodiimide.

EXAMPLE 45

5,5-Dimethyl-8-(3-methyl-2-octyl)-10-[4-(pyrrolidino)butyryloxy]-5H-[1]benzopyrano[3,4-d]pyridine hydrochloride is prepared according to the method of Example 29 by reacting equimolar quantities of 5,5-dimethyl-10-hydroxy-8-(3-methyl-2-octyl)-5H-[1]benzopyrano[3,4-d]pyridine and γ-pyrrolidinobutyric acid hydrochloride in the presence of dicyclohexyl carbodiimide.

EXAMPLE 46

5,5-Dimethyl-8-(3-methyl-2-octyl)-10-[3-(piperidino)propionyloxy]-5H-[1]benzopyrano[3,4-d]pyridine hydrochloride is prepared according to the method of Example 29 by reacting equimolar quantities of 5,5-dimethyl-10-hydroxy-8-(3-methyl-2-octyl)-5H-[1]benzopyrano[3,4-d]pyridine and β-piperidinopropionic acid in the presence of dicyclohexyl carbodiimide.

EXAMPLE 47

5,5-Dimethyl-8-(3-methyl-2-octyl)-10-[4-(thiomorpholino)butyryloxy]-5H-[1]benzopyrano[3,4-d]pyridine hydrobromide is prepared according to the method of Example 29 by reacting equimolar quantities of 5,5-dimethyl-10-hydroxy-8-(3-methyl-2-octyl)-5H-[1]benzopyrano[3,4-d]pyridine and γ-thiomorpholinobutyric acid hydrobromide in the presence of dicyclohexyl carbodiimide.

The compounds of this invention can also be prepared by the simultaneous dehydrogenation and debenzylation of the corresponding N-benzyl-1,2,3,4-tetrahydro-benzopyranopyridine as illustrated in the following example. The N-benzyl compound can be prepared according to the method described in U.S. Pat. No. 3,576,798.

EXAMPLE 48

5,5-Dimethyl-10-hydroxy-8-(3-methyl-2-octyl)-5H-[1]benzopyrano[3,4-d]pyridine

A mixture of 2.23 g. of 2-benzyl-5,5-dimethyl-10-hydroxy-8-(3-methyl-2-octyl)-1,2,3,4-tetrahydro-5H-[1]benzopyrano[3,4-d]pyridine, 0.8 g. (10%) palladium on carbon, and 100 ml. of xylene was stirred and refluxed for 24 hours. After removal of the catalyst, the filtrate was evaporated in vacuo and the residue was recrystallized from acetonitrile; m.p. 154°–156°.

EXAMPLE 49

5,5-Dimethyl-10-Methoxy-8-(3-Methyl-2-Octyl)-5H-[1]-Benzopyrano[3,4-d]Pyridine

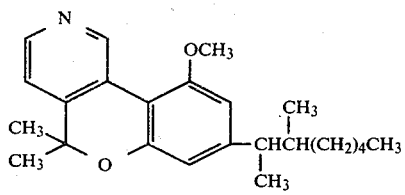

Methyl iodide (5.11 g., 0.036 mole) was added dropwise to a stirred solution of 10.59 g. (0.03 mole) of 5,5-dimethyl-10-hydroxy-8-(3-methyl-2-octyl)-5H-[1]benzopyrano [3,4-d]pyridine in 300 ml. of N,N-dimethylformamide containing 1.78 g. (0.033 mole) of sodium methoxide. The mixture was stirred at room temperature for 18 hours and 300 ml. of water was added and extracted with petroleum ether (30°-60°). The combined petroleum ether extracts were washed with water, dried with anhydrous sodium sulfate and evaporated in vacuo. The residue was purified by chromatography on a Florisil ® column with chloroform or by distillation under reduced pressure to give the pure product.

Analysis Calcd. for $C_{24}H_{33}NO_2$: C, 78.43; H, 9.05; N, 3.81. Found: C, 78.12; H, 9.19; N, 3.80.

EXAMPLE 50

5,5-Dimethyl-8-[5-(4-Fluorophenyl)-2-Pentyl]-10-Methoxy-5H-[1]Benzopyrano[3,4-d]Pyridine

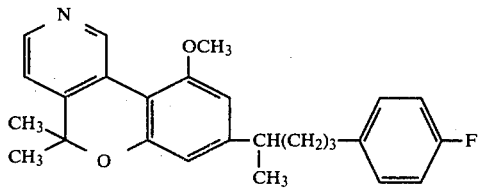

By reacting 5,5-dimethyl-8-[5-(4-fluorophenyl)-2-pentyl]-10-hydroxy-5H-[1]benzopyrano[3,4-d]pyridine with methyl iodide according to the procedure of Example 49, 5,5-dimethyl-8-[5-(4-fluorophenyl)-2-pentyl]-10-methoxy-5H-[1]benzopyrano[3,4-d]pyridine is prepared.

Analysis Calcd. for $C_{26}H_{28}FNO_2$: C, 77.01; H, 6.96; N, 3.46. Found: C, 77.23; H, 7.12; N, 3.44.

EXAMPLE 51

5,5-Dimethyl-8-(3-Methyl-2-Octyl)-10-(2-Propynyloxy)-5H-[1]Benzopyrano[3,4-d]Pyridine

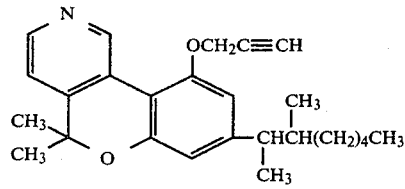

Freshly distilled 2-propynyl bromide (1.43 g., 0.012 mole) was added dropwise to a stirred solution of 3.53 g. (0.01 mole) of 5,5-dimethyl-10-hydroxy-8-(3-methyl-2-octyl)-5H-[1]benzopyrao[3,4-d]pyridine in 80 ml. of N,N-dimethylformamide containing 0.65 g. (0.012 mole) of sodium methoxide. After the addition, the mixture was stirred at room temperature for 19 hours and 80 ml. of water was added and extracted with petroleum ether (30°-60°). The combined petroleum ether extracts were washed with water, dried by anhydrous sodium sulfate and evaporated in vacuo. The residue was purified by chromatography on a Florisil ® column with chloroform to yield the pure product.

Analysis Calcd. for $C_{26}H_{33}NO_2$: C, 79.76; H, 8.50; N, 3.57. Found: C, 79.39; H, 8.53; N, 3.41.

EXAMPLE 52

5,5-Dimethyl-8-[5-(4-Fluorophenyl)-2-Pentyl]-10-(2-Propenyloxy)-5H-[1]Benzopyrano[3,4-d]Pyridine

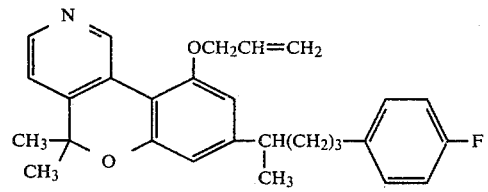

5,5-Dimethyl-8-[5-(4-fluorophenyl)-2-pentyl]-10-(2-propenyloxy)-5H-[1]benzopyrano[3,4-d]pyridine was prepared by reacting 5,5-dimethyl-8-[5-(4-fluorophenyl)-2-pentyl]-10-hydroxy-5H-[1]benzopyrano[3,4-d]pyridine with 2-propenyl bromide following the procedure of Example 51.

Analysis Calcd. for $C_{28}H_{30}FNO_2$: C, 77.93; H, 7.01; N, 3.25. Found: C, 78.56; H, 7.18; N, 3.24.

The present invention includes within its scope, pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment.

The following example further illustrates the pharmaceutical compositions which are a feature of this invention:

EXAMPLE 53

Tablets weighing 200 mg. and having the following composition are prepared by standard tableting procedures:

| Ingredient | Mg. |
| --- | --- |
| 5,5-Dimethyl-10-hydroxy-8-(3-methyl-2-octyl)-5H[1]benzopyrano[3,4-d]pyridine | 100 |
| Starch | 94 |
| Colloidal silica | 5 |
| Magnesium stearate | 1 |

It will be understood by those skilled in the art that the above composition can contain any of the compounds of this invention.

I claim:

1. A basic compound of the structure in which $R_1$ is methyl or ethyl and $R_2$ is a straight or branched alkyl of from 1–20 carbon atoms or cycloalkyl of 3 to 8 carbons; and its non-toxic pharmaceutically acceptable salts.

2. A compound in accordance with claim 1 wherein $R_2$ is an alkyl of 1 to 20 carbons or a cycloalkyl of 3 to 8 carbons and $R_3$ is hydroxy.

3. A compound in accordance with claim 2, 5,5-dimethyl-10-hydroxy-8-(3-methyl-2-octyl)-5H-[1]benzopyrano[3,4-d]pyridine.

4. A compound in accordance with claim 1 wherein $$R_2 = -Y-\text{(phenyl with } R_4, R_5, R_6\text{)}$$

and $R_3$ is hydroxy.

5. A compound in accordance with claim 4, 5,5-dimethyl-8-[5-(4-fluorophenyl)-2-pentyl]-10-hydroxy-5H-[1]benzopyrano[3,4-d]pyridine.

6. A compound in accordance with claim 1 wherein $R_3$ is an acyloxy selected from the group consisting of acetoxy, propionyloxy, and butyryloxy and $R_2$ is $$-Y-\text{(phenyl with } R_4, R_5, R_6\text{)}$$

7. A compound in accordance with claim 1 wherein $R_3$ is and $R_2$ is an alkyl of 1 to 20 carbons or a cycloalkyl of 3 to 8 carbons.

8. A compound in accordance with claim 7, 5,5-dimethyl-8-(3-methyl-2-octyl)-10-[4-(piperidino)-butyryloxy]5H-[1]benzopyrano[3,4-d]pyridine hydrochloride.

9. A compound in accordance with claim 1 wherein $$R_3 \text{ is } OC-X-N\text{(ring with }(CH_2)_a, R_9, Z, (CH_2)_b\text{)}$$

and $R_2$ is $-Y-$(phenyl with $R_4, R_5, R_6$)

10. A compound in accordance with claim 1 wherein $R_2$ is an alkyl of 1 to 20 carbons or a cycloalkyl of 3 to 8 carbons and $R_3$ is methoxy.

11. A compound in accordance with claim 10, 5,5-dimethyl-10-methoxy-8-(3-methyl-2-octyl)-5H-[1]benzopyrano[3,4-d]pyridine.

12. A compound in accordance with claim 1 wherein $R_2$ is an alkyl of 1 to 20 carbons or a cycloalkyl of 3 to 8 carbons and $R_3$ is 2-propynyloxy.

13. A compound in accordance with claim 12, 5,5-dimethyl-8-(3-methyl-2-octyl)-10-(2-propynyloxy)-5H-[1]benzopyrano[3,4-d]pyridine.

14. A compound in accordance with claim 1 wherein $R_2$ is $$-Y-\text{(phenyl with } R_4, R_5, R_6\text{)}$$

and $R_3$ is methoxy.

15. A compound according to claim 14, 5,5-dimethyl-8-[5-(4-fluorophenyl)-2-pentyl]-10-methoxy-5H-[1]benzopyrano[3,4-d]pyridine.

16. A compound in accordance with claim 1 wherein R₂ is

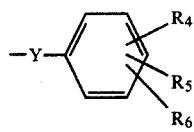

and R₃ is 2-propenyloxy.

17. A compound according to claim 16, 5,5-dimethyl-8-[5-(4-fluorophenyl)-2-pentyl]-10-(2-propenyloxy)-5H-[1]benzopyrano[3,4-d]pyridine.

18. A basic compound of the structure

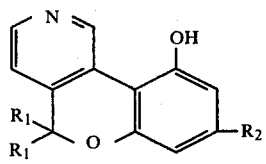

in which R₁ is methyl or ethyl and R₂ is a straight or branched alkyl of from 1–20 carbon atoms; and its non-toxic pharmaceutically acceptable salts.

19. The compounds of claim 18 in which R₂ is a branched alkyl of 5–12 carbon atoms.

20. The compounds of claim 18 in which R₂ is 1,2-dimethylheptyl together with their acid addition salts.

21. The compound of claim 20 in the form of the hydrochloride or hydrobromide salt.

22. A compound of the formula

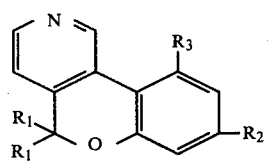

wherein each R₁ is methyl or ethyl, R₂ is a straight or branched chain alkyl of from 1–20 carbon atoms, a cycloalkyl of 3 to 8 carbons, or

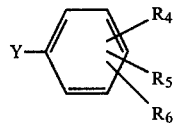

wherein Y is a straight or branched chain alkylene group having from 1 to 10 carbon atoms and each R₄, R₅ and R₆ are the same or different members of the group consisting of hydrogen or halo; R₃ is hydroxy, loweralkoxy, loweralkenyloxy, loweralkynyloxy or

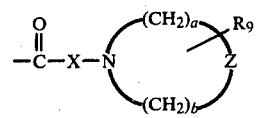

wherein X is a straight or branched chain alkylene group having from 1 to 8 carbon atoms, a is an integer from 1 to 4, b is an integer from 1 to 4, Z is CH₂, O, S or NR₁₀ with R₁₀ being hydrogen or loweralkyl, with the limitation that when Z is O or S, the sum of a and b is 3 or 4; and when Z is NR₁₀, the sum of a and b is 3–5; R₉ is hydrogen or loweralkyl, and the pharmaceutically acceptable salts thereof.

23. A compound of the formula

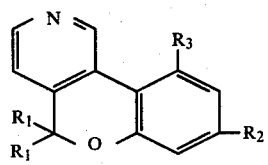

wherein each R₁ is loweralkyl, R₂ is an alkyl of 1 to 20 carbons, a cycloalkyl of 3 to 8 carbons or

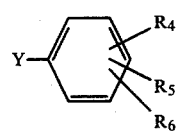

wherein Y is a straight or branched chain alkylene group having from 1 to 10 carbon atoms and each R₄, R₅ and R₆ are the same or different members of the group consisting of hydrogen, halo, trifluoromethyl or loweralkyl; and R₃ is hydroxy, loweralkoxy, loweralkenyloxy, loweralkynyloxy, or

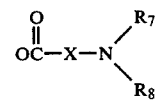

X is a straight or branched chain alkylene group having from 1 to 8 carbon atoms, and wherein R₇ and R₈ are the same or different members of the group consisting of hydrogen or loweralkyl, or

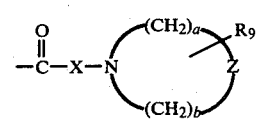

wherein X is a straight or branched chain alkylene group having from one to eight carbon atoms, a is an integer from 1 to 4, b is an integer from 1 to 4, Z is CH₂, O, S or NR₁₀ with R₁₀ being hydrogen or loweralkyl, with the limitation that when Z is O or S, the sum of a and b is 3 or 4; and when Z is NR₁₀, the sum of a and b is 3–5; R₉ is hydrogen or loweralkyl, and the pharmaceutically acceptable salts thereof.

* * * * *